United States Patent [19]

Pansiera

[11] Patent Number: 4,958,643
[45] Date of Patent: Sep. 25, 1990

[54] HINGE JOINT

[76] Inventor: Timothy Pansiera, 1050 NW. First Ave., Boca Raton, Fla. 33432

[21] Appl. No.: 367,367

[22] Filed: Jun. 16, 1989

[51] Int. Cl.$^5$ .............................................. A61F 5/00
[52] U.S. Cl. .................................. 128/80 H; 128/88;
16/286; 16/299; 16/375; 403/117
[58] Field of Search ...................... 128/80 H, 80 F, 88, 128/165, 166, 80 C; 16/286, 299, 375, 277; 403/117, 113

[56] References Cited

U.S. PATENT DOCUMENTS

| 2,591,373 | 4/1952 | Petruch | 128/80 F |
|---|---|---|---|
| 3,826,251 | 7/1974 | Ross | 128/80 F |
| 4,249,523 | 2/1981 | Bidwell | 128/88 |
| 4,252,111 | 2/1981 | Chao et al. | 128/80 F |
| 4,489,717 | 12/1984 | Moissonnier | 622/27 |
| 4,502,472 | 3/1985 | Pansiera | 128/80 F |
| 4,605,227 | 8/1986 | Hurd et al. | 128/88 |
| 4,620,532 | 11/1986 | Houswerth | 128/88 |
| 4,727,861 | 3/1988 | Yeomans et al. | 128/88 |
| 4,738,252 | 4/1988 | Friddle et al. | 128/80 C |
| 4,777,941 | 10/1988 | Borig et al. | 128/80 C |
| 4,817,588 | 4/1989 | Bledsoe | 128/80 F |

FOREIGN PATENT DOCUMENTS 0016268 10/1980 European Pat. Off. .......... 128/80 F
2181060 4/1987 United Kingdom ............ 128/80 R Primary Examiner—Edgar S. Burr
Assistant Examiner—Huong Q. Pham
Attorney, Agent, or Firm—M. K. Silverman

[57] ABSTRACT

A hinge joint includes a first planer element and a second planer element, each of said planer elements having an exterior side and an interior side. Each planer element exhibits an opening for axial rotational attachment about an end of an intermediately rotationally secured third planer element. The first and second planer elements are secured, at a defined offset by several bolts. Such offset is proportioned to permit rotation of the end of the third planer element therebetween. The interior surfaces of the first and second planer elements are provided with linear channels within which are placed springs, the function of which is to regulate the angulation and resilience of the third planer element relative to the mutually secured first and second elements of the hinge joint. Through the selective use of advancing screws within the linear channels within the interior surfaces of the first and second planer elements, the degree of compression of a spring may be selectably varied to influence the angulation and rotational characteristic of the third planer element relative to the first and second planer element and of the large mechanical parts to which the planer elements are secured.

3 Claims, 6 Drawing Sheets

HINGE JOINT

BACKGROUND OF THE INVENTION

The invention relates to a hinge joint and, more particularly, to a hinge joint having particular utility in the connection of two otherwise, separate thermoformed elements which are parts of a larger mechanical system, for example, an orthopedic brace.

In such an application, it is desirable to imbed normally fixed elements of a hinge joint within the thermoplastic material of parts of the larger system to ensure that the hinge will not move, or work loose, relative to the thermoplastic pieces to which it is attached.

The present hinge joint defines an improvement over the prior art in that the hinge joint disclosed herewith may be easily assembled from metal stampings and bolted together, whereas the prior art requires the use of metal castings to perform the same function. Such cast metal hinges are both expensive to produce and add unnecessary weight to the associated structure. Also, as may be appreciated, any object formed of cast metal cannot be readily bent. In many applications, including the area of orthopedic braces, the ability to bend the hinge (as well as other parts of the assembly) is an important factor to the orthopedic technician attempting to customize the orthopedic device to the needs of the patient.

Further in the use of the inventive hinge joint, described below, the production of an orthopedic brace incorporates the positioning of the inventive hinge joint as an integral part thereof, as opposed to, in the prior art, the addition of a cast metal hinge over or under larger surfaces of the system after they have been completely formed.

There does not, to the knowledge of the inventor, exist relevant printed or patented information to the invention herein.

SUMMARY OF THE INVENTION

The present invention comprises a hinge joint comprising a first planer element and a second planer element, each of said planer elements having an exterior side and an interior side. Each planer element exhibits an opening for axial rotational attachment within an end of an intermediately rotationally secured third planer element therebetween. Said first and second planer elements are secured, at a defined offset therebetween, by a plurality of bolts. Such offset is proportioned to permit rotation of said end of said third planer element. Said interior surfaces of said first and second planer elements are provided with linear channels within which are placed springs, the function of which is to regulate the angulation and resilience said third planer element relative to said mutually secured first and second elements of the hinge joint. Through the selection use of advancing screws within said linear channels within said interior surfaces of said first and second planer elements, the degree of compression of said springs may be selectably varied to thereby influence the angulation and rotational characteristic of said third planer element relative to said first and second planer elements and, thereby, of the larger mechanical parts to which said planer elements are secured. In a preferred use, each of said planer elements are formed integrally within thermoplastic parts of a larger mechanical system.

It is accordingly an object of the present invention to provide a hinge joint having reduced cost, reduced weight, and greater ease of usage than is the case with hinge joints known in the prior art.

It is another object to provide a hinge joint having particular utility in the construction of mechanical systems having thermoplastic parts in relative rotational relationship to each other.

It is a further object of the present invetion to provide a hinge joint particularly adapted for use in orthopedic braces and the like.

The above and yet other objects and advantages of the present invention will become apparent in the hereinafter set forth Detailed Description of the Invention, the Drawings, and Claims appended herewith.

DETAILED DESCRIPTION OF THE INVENTION

Figure 1:
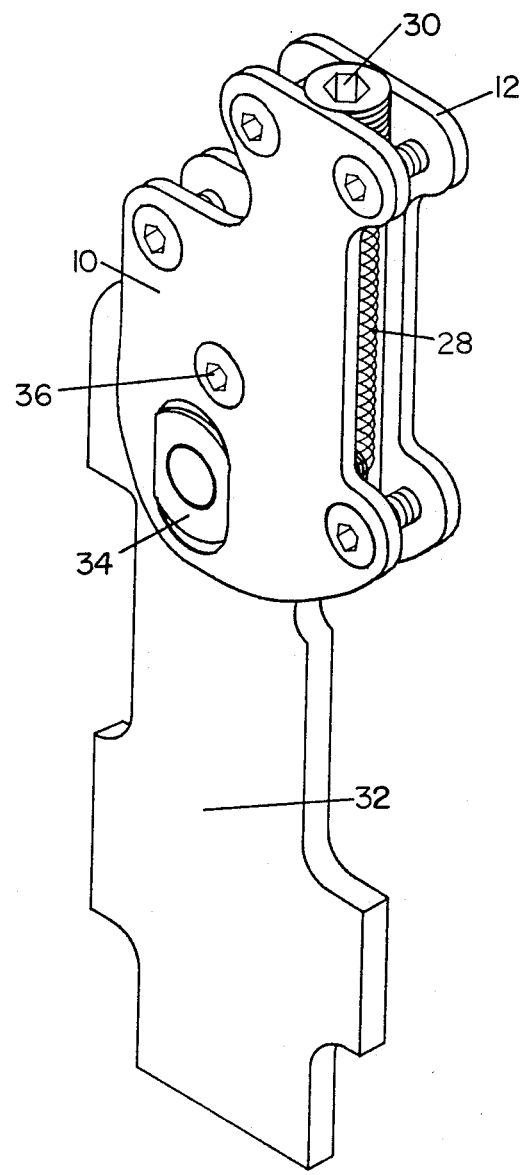
FIG. 1 is a perspective view of the inventive hinge joint.
Figure 2:
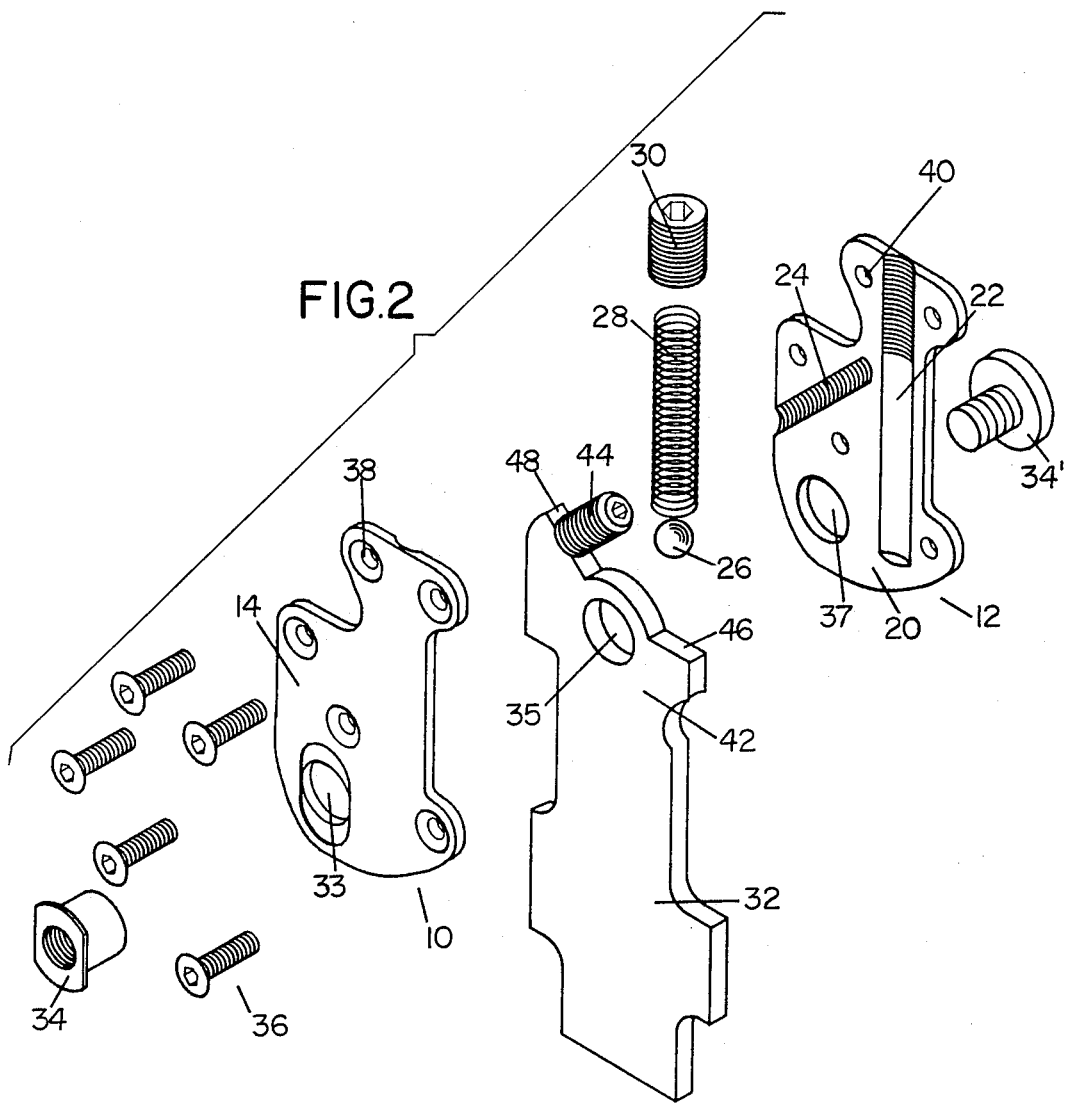
FIG. 2 is an exploded view of the hinge joint.
Figure 3:
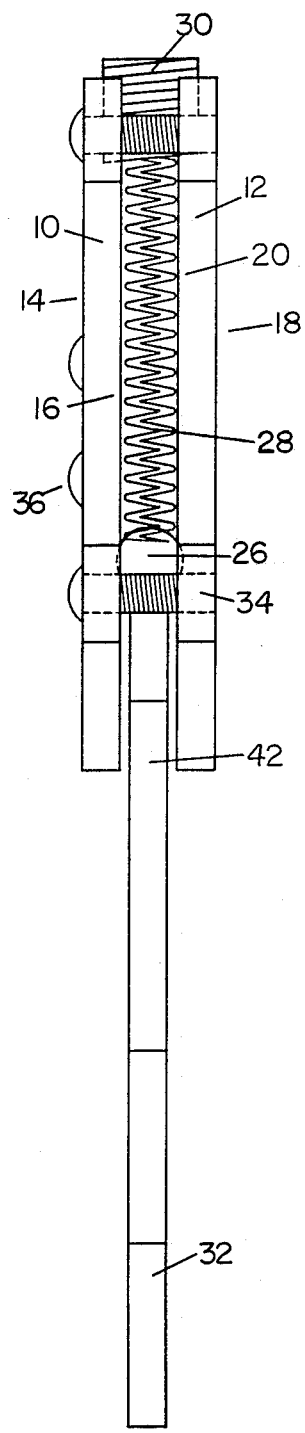
FIG. 3 is an end view thereof.

With reference to the views of FIGS. 1 thru 3, the inventive hinge joint may be seen to include a first planer element 10 and a second planer element 12, each of which elements exhibit an exterior side and an interior side. More particularly, said first planer element exhibits an exterior side 14 and an interior side 16, while said second planer element exhibits exterior side 18 and interior side 20.

As may be noted in the exploded view of FIG. 2, the interior side of said first and second planer elements includes linear channels 22 and 24. Said linear channel 22 includes, therein, a ball bearing 26, a spring 28, and a control screw 30, the purpose of which combination of elements is to regulate the rotational and resilient characteristics of a third planer element 32 relative to the structure formed by the combination of said first and second planer elements 10 and 12 when said elements are secured about said third element 32 by an axis securement nut and bolt 34 which are placed through aligned opening 33 of element 10, opening 35 of end 42 of third element 32, and opening 37 of element 12.

An uniform offset between first and second planer elements 10 and 12 is defined through the use of a plurality of Allen-head bolts 36 which pass through openings 38 and 40 of said first and second elements 10 and 12 respectively. Said Allen-head bolts 36 define an offset between said planer elements 10 and 12 which permits rotation of said end 42 of the third planer element 32. Also, the offset defined by said Allen-head bolts 34 is of importance in providing a cavity into which molten and semi-molten thermoplastic material may enter in order to integrate the inventive hinge joint into the plastic of a mechanical part formed of such thermoplastic material, as is later described below.

With reference to FIG. 3, the interior surfaces of the first and second planer elements are provided with a second linear channel 24 into which is placed a control screw 44. Accordingly, it may be appreciated that two modes of control of the orientation and resiliency of the combination of said first and second elements relative to said intermediately rotationally secured third element 32 is obtained. As regard to the first mode, there is provided a spring-loaded resilient mechanical force applied within channel 22. As regard to the second mode, within said channel 24 is provided an Allen-head control screw 44. As may be appreciated, the rotational advance of Allen-head nut 30 within linear channel 22 will increase clock-wise rotational spring force against surface 46 of end 42 of the third planer element 32, while the advance of Allen-head control screw 44 within linear channel 24 will change, in the clockwise direction, the operational orientation (the angulation) of the axis of third element 32 relative to the axis of linear channel 22 of said first and second planer elements 10 and 12. Accordingly, Allen-head screw 44 comprises a polar positioning means for orienting lower element 32 relative to the combined structure of said first and second elements, while the assembly of said elements 26, 28, and 30 comprise a biasing means which selectably defines the degree of rotational resilience of lower element 32 relative to the combination of first and second elements 10 and 12.

As may be appreciated from the geometry of the elements 10, 12 and 32 of the inventive hinge joint, such elements may be readily formed of metal stampings and, in the manner set forth above, are readily assembled through the use of axis securement nut and bolt 34, and said Allen-head screws 36. As such, the consequential structure of a cast metal hinge joint is obtained without the associated cost or weight. Also, elements 10, 12 and 32 may be bent to accommodate special requirements associated with certain applications of the instant joint such as in an orthopedic brace.

Figure 4:
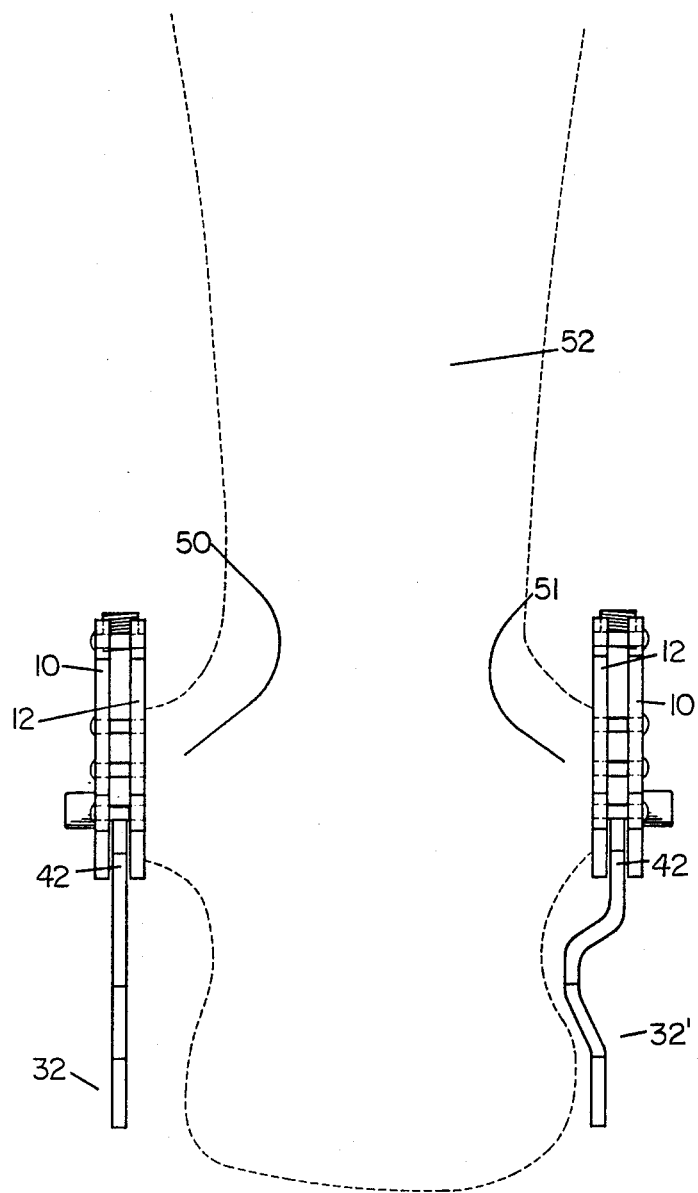
FIG. 4 is a view of the hinge joint mounted to a mannequin after removal of a plaster material, between the joints and the mannequin.

In FIG. 4 the hinge joint is shown mounted upon the leg of a mannequin prior to subsequent steps associated with the production of the orthopedic brace. In this view, it may be appreciated that a lower element 32' may comprise any of a number of shapes provided end 42 is able to mate between planer elements 10 and 12 of the hinge joint. In FIG. 4 one may further note that the hinge joints have been offset distances 50 and 51 from the mannequin leg 52 and, as well, offset distances 50 and 51 act to mutually selectably orient the planes defined by the parallel surfaces of the sets of elements 10 and 12, in a desired orientation relative to each other.

Figure 5:
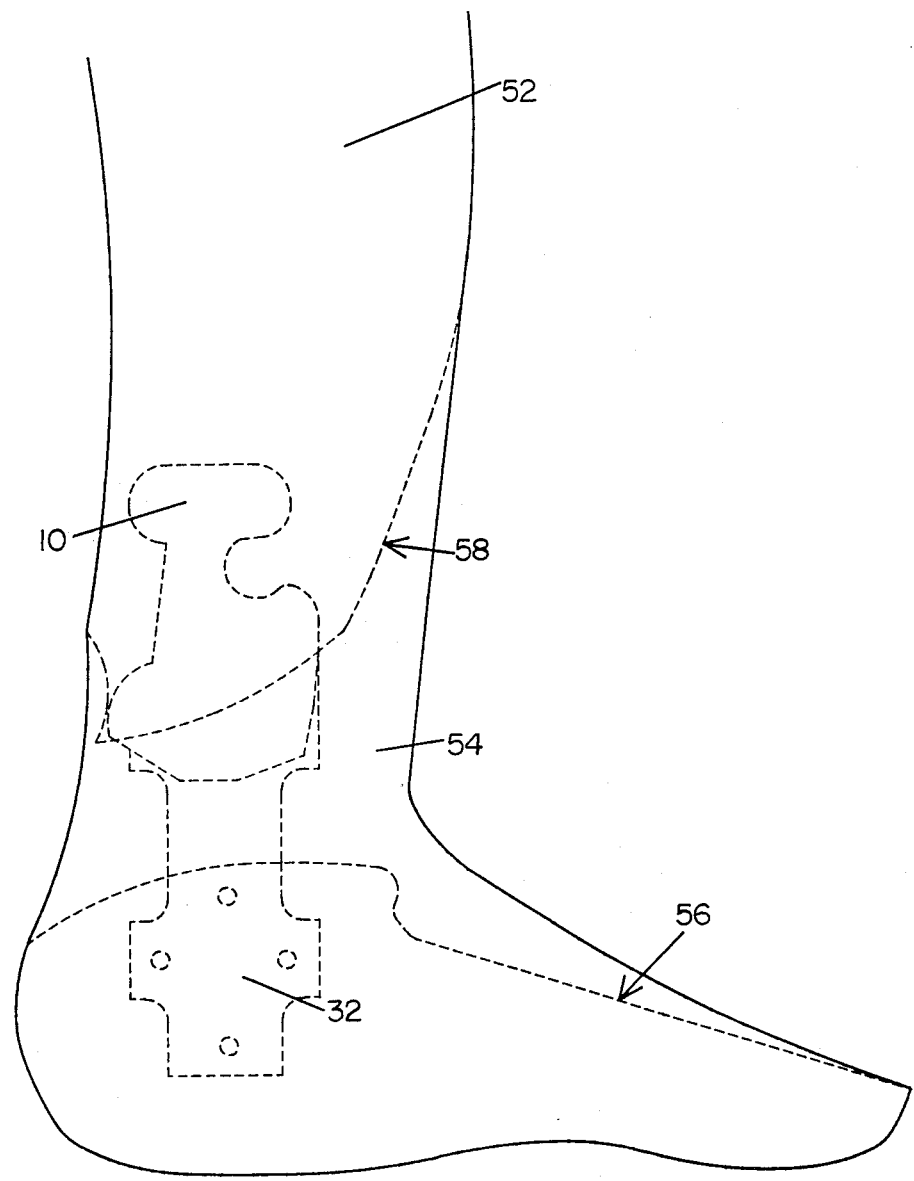
FIG. 5 is a view showing a vacuum-formed thermoplastic layer positioned over the hinge joint and about the mannequin.
Figure 6:
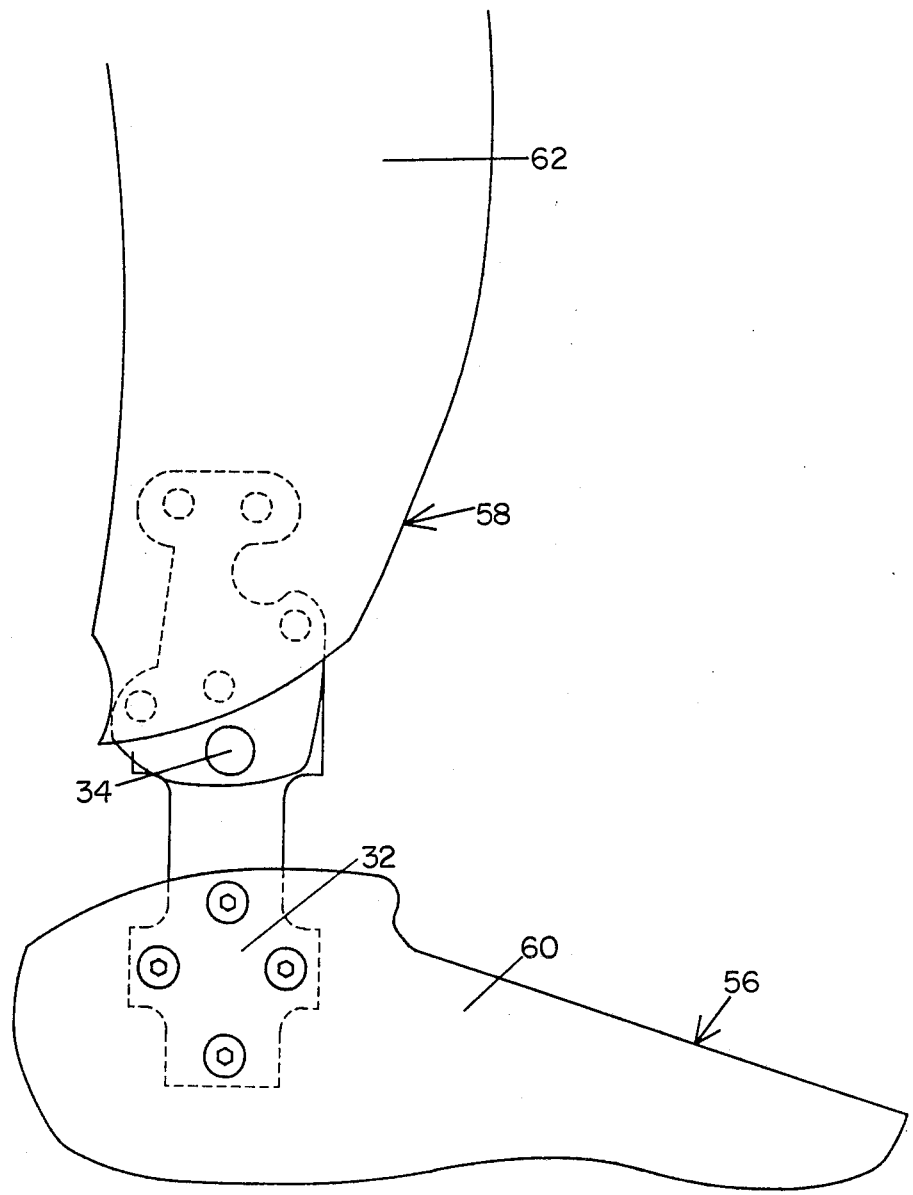
FIG. 6 is a perspective view showing the hinge joint embedded within the vacuum-formed thermoplastic layer, after the thermoplastic layer has been selectably cut to define the desired shape of a brace.

In the view of FIG. 5 there is schematically shown the application of a layer of thermoplastic material 54 over mannequin leg 52. Therein, it should be noted that both elements 10 and 12, and lower element 32, are completely covered by the layer 54 of thermoplastic material and, as well, said elements are completely embedded therein such that the thermoplastic material will enter the volume of the cavity formed between the offset separating the first and second flat planer elements 10 and 12. It is to be understood that during said thermoforming step, dummy elements in the nature of wooden cylinders, are placed within said linear channels 22 and 24 to prevent the entrance of the thermoplastic of other material into said linear channels. This permits the thermoplastic layer 52 to completely surround the inventive hinge joint and, thereby, permit the hinge joint to become embedded therewith. After the structure shown in FIG. 5 is hardened, the thermoplastic material is cut along lines 56 and 58 to define the outline of the mechanical parts of, in the illustrated application, an orthopedic brace. The resultant structure of FIG. 6 is that of a vacuum formed orthopedic brace in which the joint elements thereof, apart from the rotational surfaces thereof, are completely embedded within the thermoplastic material of which the brace is formed. As may be noted in the views of FIGS. 5 and 6, lower, third planer element 32 may either be riveted into lower orthopedic part 60 or may be surrounded by the thermoplastic material 52 of which part 60 is made.

In the view of FIG. 6, it is seen that rotational coupling of nut and bolt 34 is left free (of the thermoplastic) to operate, thereby permitting the lower mechanical part 60 to which lower element 32 is attached to enjoy the rotational characteristics of polar position and polar resiliency relative to upper part 62 of the orthopedic structure, which is afforded by the operation of the biasing means within said linear channels 22 and 24.

Accordingly, while there has been shown and described the preferred embodiment of the present invention, it is to be appreciated that the invention may be embodied otherwise than is herein specifically shown and described, and that within said embodiment, certain changes may be made in the details thereof without departing from the underlying principles of this invention within the scope of the claims appended herewith.

Having thus described my invention, what I claim as new, useful and non-obvious and, accordingly secure by Letter Patent of the United States is:

1. A hinge joint, comprising:
   (a) a first planer element having therein a transverse rotational opening, said first planer element having an exterior and an interior surface, said interior surface including respective semi-cylindrical halves of a first linear channel and a second linear channel;
   (b) a second planer element having therein a transverse rotational opening, said second planer element having an interior and an exterior surface, said second planer element being substantially symmetrical to said first planer element under the respective of interior surfaces of said planer elements are oriented as opposing falls to each other, said interior surface of said second planer element provided with respective semi-cylindrical halves of said first and second linear channels formed in said interior surface of said second planer element;
   (c) a third planer element having a transverse axial opening on one end thereof, said end thereof proportioned for planer orientation between said interior surfaces of said first and second planer elements;
   (d) means for securing said first and second planer elements at a uniform offset from each other;
   (e) rotational coupling means for securement in said axial openings of said first, second and third planer elements, in which, when said coupling means is secured, said third planer element is rotationally moveable within the offset of the combination of said first and second planer elements;
   (f) in said first linear channel formed by the combination of said semi-cylindrical halves of said first and second planer elements, means for selectably changing the angulation of a longitudinal axis of said third element relative to those axes defined by said first and second linear channels of said respective first and second planer element, said selectable changing means operating in a first rotational direction relative to an axis of said axial opening; and (g) within said second linear channel, means for resiliently biasing, in a rotational direction opposite to that of said angulation changing means of said first channel, the rotational characteristic of said third planer element relative to the combination of said first and second planer elements.

2. The hinge joint as recited in claim 1 in which said angulation changing means comprises the combination of an Allen-head screw threadably advancable within said second linear channel.

3. The hinge joint as recited in claim 1 in which said means for selectably resiliently biasing comprises the combination of a ball-bearing in rotational communication with an opposing end of said third element, a linear compression spring said ball-bearing, and an Allen-head screw threadably advancable against an opposite end of said compressing spring and within said first linear channel.

* * * * *